United States Patent
Wanders et al.

(10) Patent No.: US 7,923,520 B2
(45) Date of Patent: Apr. 12, 2011

(54) HIGH REFRACTIVE INDEX MONOMERS AND (CO)POLYMERS PREPARED THEREFROM

(75) Inventors: Bernardus Franciscus Maria Wanders, Angerlo (NL); Henk Haitjema, Eerbeek (NL)

(73) Assignee: Procornea Holding B.V., Eerbeek (NL)

( * ) Notice: Subject to any disclaimer, the term of this patent is extended or adjusted under 35 U.S.C. 154(b) by 283 days.

(21) Appl. No.: 12/279,520

(22) PCT Filed: Feb. 14, 2007

(86) PCT No.: PCT/NL2007/050058
§ 371 (c)(1),
(2), (4) Date: Aug. 14, 2008

(87) PCT Pub. No.: WO2007/094664
PCT Pub. Date: Aug. 23, 2007

(65) Prior Publication Data
US 2009/0023879 A1    Jan. 22, 2009

Related U.S. Application Data

(60) Provisional application No. 60/772,893, filed on Feb. 14, 2006.

(30) Foreign Application Priority Data

Feb. 14, 2006 (EP) .................................... 06101662
Mar. 9, 2006 (EP) .................................... 06110902

(51) Int. Cl.
*C08F 12/34* (2006.01)
*A61F 2/16* (2006.01)

(52) U.S. Cl. ........ 526/326; 526/286; 526/319; 526/320; 526/328; 623/6.56; 623/6.58

(58) Field of Classification Search .................. 526/286, 526/319, 328, 320, 326; 623/6.56, 6.58
See application file for complete search history.

(56) References Cited

U.S. PATENT DOCUMENTS

| | | | | |
|---|---|---|---|---|
| 5,132,430 A | * | 7/1992 | Gaudiana et al. | 548/444 |
| 5,861,031 A | * | 1/1999 | Namdaran et al. | 623/6.56 |
| 6,140,438 A | | 10/2000 | Ojio et al. | |
| 2003/0130460 A1 | | 7/2003 | Freeman et al. | |
| 2003/0224250 A1 | | 12/2003 | Setthachayanon et al. | |
| 2005/0049376 A1 | | 3/2005 | Chisholm et al. | |

* cited by examiner

*Primary Examiner* — Ling-Siu Choi
*Assistant Examiner* — Vu A Nguyen
(74) *Attorney, Agent, or Firm* — Gilberto M. Villacorta; Sunit Talapatra; Foley & Lardner LLP

(57) ABSTRACT

The present invention relates to high refractive index monomers according to formula (I) and (co)polymers comprising such high refractive index monomers. The 5 (co)polymers are highly suitable for the manufacture of optical articles, in particular flexible optical articles, more in particular intraocular lenses.

(I)

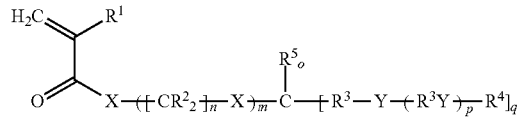

24 Claims, No Drawings

HIGH REFRACTIVE INDEX MONOMERS AND (CO)POLYMERS PREPARED THEREFROM

The present invention relates to high refractive index monomers and (co)polymers comprising such high refractive index monomers. The (co)polymers are highly suitable for the manufacture of optical articles, in particular intraocular lenses.

BACKGROUND OF THE INVENTION

With the recent advances in small-incision cataract surgery, increased emphasis has been placed on developing soft, foldable materials suitable for use in artificial intraocular lenses ("IOL"). Materials that are commonly used for such lenses include hydrogels, silicones and acrylic polymers.

Hydrogels have a relatively low refractive index which makes them less desirable materials because of the thicker lens optic that is necessary to achieve a given refractive power. Silicones have a higher refractive index than hydrogels, but tend to unfold explosively after being placed in the eye in a folded position. Explosive unfolding can potentially damage the corneal endothelium and/or rupture the natural lens capsule. Acrylic polymers are currently the material of choice since they typically have a high refractive index and unfold more slowly or controllably than silicone materials.

An important feature in the design of modern IOL's made of high refractive index material is that lenses can be made thinner which allows for a specific design of the lens being rolled in smaller dimensions. This consequently necessitates a smaller incision size in lens cataract surgery with the advantage of reduced risks for complications like astigmatism or complications related to incision healing.

A further requirement for IOL material is that rolling the lens does not induce tears or wrinkles so that after release of the lens from the cartridge nozzle the lens unfolds in a controlled way to its prerolled dimensions without its optical quality being compromised. The material must also be stiff enough such that thin high refractive index lenses do not deform when residing in the eye. After all, lenses must remain flat to retain their optical properties.

U.S. Pat. No. 5,290,892 discloses high refractive index, acrylic copolymers suitable for use as an IOL material. These acrylic copolymers comprise acrylate monomers, methacrylate monomers and a cross-linking monomer. Preferably, the copolymer has a glass transition temperature of about 20° to 25° C., an elongation of at least 150%. The refractive index at 20° C. of the copolymers disclosed in the Examples are not higher than 1.5584 (Example 10).

U.S. Pat. No. 5,331,073 discloses acrylic copolymers suitable for use as IOL materials. These copolymers comprise two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking monomer. Example 3 discloses a copolymer having an elongation of 143% and a refractive index of 1.55.

U.S. Pat. No. 5,693,095 and EP A 485.197 disclose copolymers that are suitable as IOL materials. These copolymers comprise a hydrophilic monomer and an aryl acrylic hydrophobic monomer having the general formula:

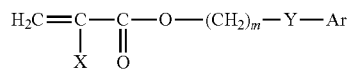

wherein X is hydrogen or methyl, m is an integer of 0-6, Y is a direct bond, O, S or NR(R may be alkyl) and Ar is an optionally substituted aromatic group. The copolymers have preferably a refractive index of at least 1.50, a glass transition temperature of −20° to 25° C. and an elongation of at least 150%. The examples show a highest refractive index of 1.544.

U.S. Pat. No. 6,140,438 discloses an IOL material comprising a copolymer of a hydrophilic monomer, an alkyl(meth)acrylate wherein the alkyl group has 1-20 carbon atoms, and an aromatic ring containing (meth)acrylate monomer of the formula:

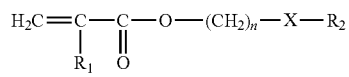

wherein $R_1$ is hydrogen or methyl, n is an integer of 0-5, X is a direct bond or oxygen, and $R_2$ is an optionally substituted aromatic group. The copolymer has a water absorptivity of 1.5 to 4.5 wt. % and has an improved transparency.

The copolymers disclosed above all comprise at least two acrylic monomers and a cross-linking monomer. However, the required use of two acrylic monomers to adjust the glass transition temperature to around ambient temperature or below (as otherwise the lenses cannot be folded without damaging the lens) has the disadvantage that the refractive index is also lowered.

U.S. Pat. No. 6,653,422 discloses acrylic monomers of the formula:

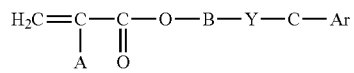

wherein it is preferred that A is hydrogen or methyl, B is —$(CH_2)_m$— wherein m is an integer of 2-5, Y is a direct bond or oxygen, C is —$(CH_2)_w$— wherein w is an integer of 0 or 1 and Ar is phenyl. The IOL material is made from these monomers only and a cross-linking monomer. The refractive index is at least 1.50, de glass transition temperature is preferably below 25° C. and the elongation is at least 150%. According to the examples, the copolymer made of 3-benzoyloxypropyl methacrylate (B=3, Y=O, w=1, Ar=phenyl) and polyethylene glycol 1000 dimethyacrylate has the highest refractive index (dry state) which is 1.543 (Example 11).

US 2005/0049376 discloses curable (meth)acrylate compositions suitable for optical articles and in particular for light management films. Apart from a high refractive index, these compositions when cured have desirably a high glass transition temperature for shape retention during storage and use of the light management films. Tables 7 and 8 disclose glass transition temperatures of 41°-62° C. The refractive index of a composition made of 1,3-bis(thiophenyl)propane-2-yl acrylate and the diacrylate of tetrabromo bisphenol A diepoxide has a refractive index as high as 1.6016 (Example 14). Although generally having a high refractive index, the compositions are obviously unsuitable for IOL's because of their high glass transition temperatures. U.S. Pat. No. 6,833,391 also discloses high refractive index monomers.

It is therefore an object of the invention to provide acrylate compositions having a high refractive index as well as a low glass transition temperature, in particular a glass transition temperature of lower than 25° C., so that they are suitable for the manufacture of IOL's, in particular flexible IOL's.

SUMMARY OF THE INVENTION

The present invention relates to a high refractive index monomer according to formula (I):

$$H_2C \diagup\!\!\!\diagdown R^1 \quad O = \diagdown\!\!\!\diagup X-(\!(CR^2_2)_n-X)_m-\overset{R^5_o}{\underset{|}{C}}-(\!(R^3-Y-(R^3Y)_p-R^4)_q$$ (I)

wherein:
R$^1$ is H or CH$_3$;
X is O or S;
R$^2$ is independently H or linear or branched C$_1$-C$_6$ alkyl;
n=3 to 10;
m=1-10;
R$^3$ is linear or branched C$_1$-C$_3$ alkylene;
Y is O or S;
p=0-5;
R$^4$ is C$_6$-C$_{18}$ aryl or heteroaryl;
q is 2 or 3;
o is 0 or 1;
when q=2, then o is 1;
when q=3; then o is 0; and
R$^5$ is independently H or linear or branched C$_1$-C$_6$ alkyl.

The present invention also relates to a polymer composition comprising a (co)polymer obtainable by polymerizing or copolymerizing, optionally together with a cross-linking monomer, the high refractive index monomer according to formula (I). The present invention further relates to optical articles, in particular intraocular lenses, comprising these polymer compositions.

DETAILED DESCRIPTION OF THE INVENTION

According to the present invention, the following definitions apply.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

An alkyl group is to be understood as a linear or branched alkyl group e.g. having 1 to 6 carbon atoms. Examples of such alkyl groups include methyl, ethyl, 1-propyl, 2-propyl, 1-butyl, 2-butyl, 1-pentyl, 1-hexyl and the like.

An alkylene group is to be understood as a linear or branched alkylene group having 1 to 3 carbon atoms, e.g. 1,3-propanediyl (—CH$_2$—CH$_2$—CH$_2$—) and ethanediyl (—CH$_2$—CH$_2$—).

An aryl group is to be understood as an aryl group having 6 to 18 carbon atoms. The aryl group may be substituted or unsubstituted. If the aryl group is substituted, it is preferred that the aryl group is substituted with 1 to 5 substituents, preferably 1 to 3 substituents, selected from the group consisting of halo, C$_1$-C$_4$ alkyl, C$_1$-C$_4$ alkyl-O—, C$_1$-C$_4$ alkyl-S—, C$_1$-C$_4$ haloalkyl, C$_1$-C$_4$ haloalkyl -O— and C$_1$-C$_4$ haloalkyl-S—. The aryl group may also be an annelated aryl group such as naphtyl and anthracenyl.

A heteroaryl group is to be understood as an aryl group having 6 to 18 carbon atoms and comprising 1 to 3, preferably 1 to 2 heteroatoms selected from the group consisting of nitrogen, oxygen and sulphur. Suitable examples of heteroaryl groups include imidazolyl, furanyl, isoxazolyl, pyranyl, pyrazinyl, pyrazolyl, pyridyl and the like. For the nomenclature of heteroaryl groups, reference is made to Handbook of Chemistry & Physics, 59$^{th}$ Ed., CRC Press, Boca Raton, Fla., 1978-1979. The heteroaryl group may also be an annelated heteroaryl group such as indolyl and benzothiazolyl.

According to the invention, it is preferred that n is 3-5. Most preferably n is 3. It is also preferred that m=1-5, more preferably 1-4, most preferably 1-3.

It is furthermore preferred that in the high refractive index monomer according to formula (I) X is O.

Additionally, it is preferred that Y is S.

According to the present invention, it is also preferred that p is 0.

Furthermore, q is preferably 2 and o is then 1.

According to the invention, it is preferred that in the high refractive index monomer according to formula (I) R$^5$ is H.

R$^4$ is preferably an unsubstituted aryl group and is more preferably phenyl.

A preferred group of high refractive index monomers is represented by formula (II):

$$H_2C \diagup\!\!\!\diagdown R^1 \quad O = \diagdown\!\!\!\diagup X-(\!(CR^2_2CR^2_2-X)_a-\overset{R^5_c}{\underset{|}{C}}-(\!(R^3-Y-(R^3Y)_d-R^4)_b$$ (II)

wherein:
R$^1$ is H or CH$_3$;
X is O or S;
R$^2$ is independently H or linear or branched C$_1$-C$_6$ alkyl;
a=1 to 5;
R$^3$ is linear or branched C$_1$-C$_3$ alkylene;
Y is O or S;
d=0-5;
R$^4$ is C$_6$-C$_{18}$ aryl or heteroaryl;
b is 2 or 3;
c is 0 or 1;
when b=2, then c is 1;
when b=3; then c is 0; and
R$^5$ is independently H or linear or branched C$_1$-C$_6$ alkyl.

In the high refractive index monomers according to formula (II), it is preferred that a is 1 or 2.

It is furthermore preferred that in the high refractive index monomer according to formula (II) X is O. Additionally, it is preferred that Y is S. It is also preferred that d is 0. Furthermore, b is preferably 2 and c is then 1. It is also preferred that in the high refractive index monomer according to formula (II) R$^5$ is H.

R$^4$ is preferably an unsubstituted aryl group and is more preferably phenyl.

Another preferred group of high refractive index monomers is represented by formula (III):

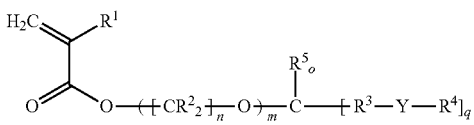

(III)

wherein $R^1$, $R^2$, $R^3$, $R^4$, $R^5$, Y, n, m, o and q are as defined above. Most preferably, Y is S.

Yet another preferred group of high refractive index monomers is represented by formula (IV):

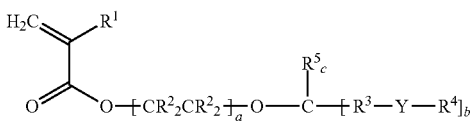

(IV)

wherein $R^1$, $R^2$, $R^3$, $R^4$, $R^5$, a, b and c are as defined above.

An even more preferred group of highly refractive index monomers is represented by formula (V):

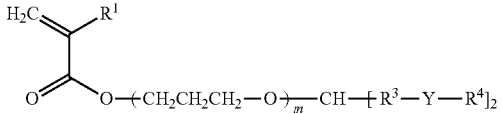

(V)

wherein $R^1$, $R^3$ and $R^4$ and m are defined as above. In formula (III), it is preferred that Y is S and $R^4$ is phenyl. According to another preferred embodiment, it is preferred that $R^3$ is —$CH_2$—. According to yet another preferred embodiment, it is preferred that m=1. According to a most preferred embodiment, Y is S, $R^4$ is phenyl, $R^3$ is —$CH_2$— and m=1.

Another even more preferred group of highly refractive index monomers is represented by formula (VI):

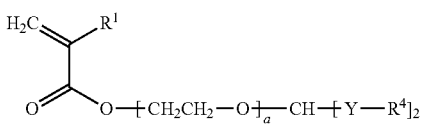

(VI)

wherein $R^1$, $R^4$ and a are defined as above. In formula (VI), it is preferred that a is 1 or 2. It is also preferred that in formula (VI) Y is S and $R^4$ is phenyl.

An example of a most preferred embodiment of the highly refractive index monomers according to the present invention is shown in formula (VII):

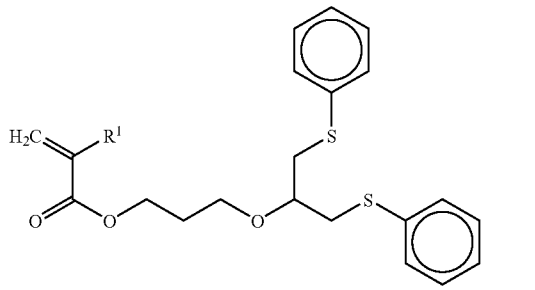

(VII)

The present invention further relates to (co)polymers and polymer compositions obtainable by polymerizing or copolymerizing a high refractive index monomer according to formula (I). Such (co)polymers and polymer compositions are characterized by having a glass transition temperature $T_g$ of less than 25° C. thereby making these (co)polymers and polymer compositions very suitable for the manufacture of optical articles, in particular intraocular lenses.

The (co)polymers may be homopolymers that are crosslinked. In this patent application the term "homopolymers" is to be understood as consisting of a single device forming monomer, i.e. the monomer according to formula (I), whereas the term "copolymers" is to be understood as comprising at least two device forming monomers, one of which is the high refractive index monomer according to formula (I). The term "device forming monomer" is disclosed in U.S. Pat. No. 6,653,422, incorporated by reference herein for the US patent practice, and can be referred to as a lens-forming monomer, in particular an IOL-forming monomer. Both the homopolymers and copolymers according to this invention also comprise a crosslinking monomer as will be discussed below.

In the copolymers according to the present invention, the at least second monomer is preferably a second acrylate monomer. In this document, the term "acrylate monomer" is to be understood as comprising acrylates, methacrylates and mixtures thereof.

The second acrylate monomer is preferably represented by formula (VIII):

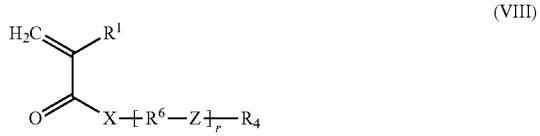

(VIII)

wherein:
$R^1$ and $R^4$ are as defined above;
$R^6$ is substituted or unsubstituted $C_1$-$C_6$ alkylene;
X is as defined above;
Z is O, S or a direct bond; and
r is 0, 1, 2 or 3.

$R^6$ may be substituted by one or more halo, $C_1$-$C_4$ alkyl, $C_1$-$C_4$ alkyl-O—, $C_1$-$C_4$ alkyl-S—, $C_1$-$C_4$ haloalkyl, $C_1$-$C_4$ haloalkyl-O— and $C_1$-$C_4$ haloalkyl-S—.

According to a preferred embodiment of the present invention, the crosslinking monomer is a multifunctional (meth)acrylate monomer which comprises at least two (meth)acrylate moieties. According to this embodiment, the crosslinking monomer is represented by the general formula (IX):

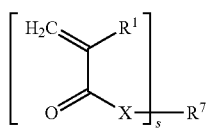

(IX)

wherein:
$R^1$ is H or $CH_3$;
$R^7$ is substituted or unsubstituted $C_1$-$C_{300}$ alkyl, aryl, alkaryl, arylalkyl or heteroaryl;
X is as defined above; and
s=2, 3 or 4.

If substituted, the substituents of $R^7$ are preferably selected from the group consisting of halo, $C_1$-$C_4$ alkyl, $C_1$-$C_4$ haloalkyl, $C_1$-$C_4$ alkyl-O—, $C_1$-$C_4$ alkyl-S—, $C_1$-$C_4$ haloalkyl-O—, $C_1$-$C_4$ haloalkyl-S— and OH—.

Suitable examples are e.g. disclosed in U.S. Pat. No. 6,653, 422 which is incorporated by reference for the US patent practice.

According to another preferred embodiment of the present invention, the cross-linking monomer is a dendritic, star or hyperbranched (co)polymer having terminal OH end groups that are partly or completely esterified with (meth)acrylic acid. For example, three arm to six arm polyethoxylates are known in the art wherein trimethylolpropane, pentaerythritol or trimethylol propane ethoxylate are used as the core. Another example is the Boltorn polymer series, in particular H20, H30 and H40, that are manufactured by Perstorp AB.

According to a yet another preferred embodiment of the invention, the crosslinking monomer is selected from the group consisting of terminally ethylenically unsaturated compounds having more than one unsaturated group, preferably a (meth)acrylate group. Suitable cross-linking monomers according to this preferred embodiment of the present invention include:
ethylene glycol dimethacrylate;
diethylene glycol dimethacrylate;
allyl methacrylate;
2,3-propanediol dimethacrylate;
1,4-butanediol dimethacrylate;
$CH_2$=$C(CH_3)C$(=O)O—$(CH_2CH_2O)_t$—C(=O)$C(CH_3)$=$CH_2$ where t=1-50; and
$CH_2$=$C(CH_3)C$(=O)O$(CH_2)_u$O—C(=O)$C(CH_3)$=$CH_2$ where u=3-20; and their corresponding (meth)acrylates.

The more preferred crosslinking monomer according to this preferred embodiment of the invention is represented by formula (X), wherein s is such that the number-average molecular weight is about 500 to about 2000:

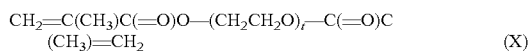

(X)

However, according to the invention it is most preferred that t is 1-5.

Generally, only one crosslinking monomer will be present in the polymer compositions, homopolymers and copolymers of the present invention. However, combinations of crosslinking monomers may be desirable.

The polymer compositions, the homopolymers and copolymers according to the present invention are prepared by methods well known to the person skilled in the art. For example, the desired components may be mixed to produce a homogeneous monomer mixture that in a subsequent step is polymerized, preferably in the presence of a catalyst, preferably a radical initiator or a photo initiator, or by irradiation, preferably UV/VIS-irradiation (also known in the art as "blue-light irradiation", i.e. light having a wave length of more than about 390 nm). Prior to the polymerization reaction, the monomer mixture may be degassed to remove any air present by applying a vacuum or the like. The polymerization is usually conducted in a mould.

Generally, the total amount of the crosslinking monomer in the monomer mixture is at least 0.1% by weight and, depending on the identity and concentration of the remaining components and the desired physical properties, can range to about 20% by weight, based on the total weight of the monomer composition. The preferred concentration range for the crosslinking monomer is 0.1-15% by weight, based on the total weight of the homogeneous monomer mixture.

In addition to the monomers and crosslinking monomers disclosed above, the polymer composition according to the present invention may contain a total of up to about 10% by weight of additional components, based on the total weight of the monomer mixture, which serve other purposes, such as reactive UV, UV/VIS and/or blue-light absorbers.

Suitable free-radical initiators are for example peroxy free-radical initiators, e.g. t-butyl-(peroxy-2-ethyl) hexanoate and di(tert-butylcyclohexyl) peroxydicarbonate and azo compounds such as AIBN. Suitable photo initiators are benzoylphosphine oxide photoinitiators, such as the blue-light initiator 2,4,6-trimethyl-benzoyldiphenylphosphine oxide. Initiators are usually present in an amount of about 5% (weight) or less, based on the weight of the monomer mixture.

The present invention also relates to the use of the polymer composition for producing optical articles, in particular intraocular lenses. The cured polymer composition that is used as the material for the manufacture of the optical article, in particular the intraocular lens, has preferably a refractive index of at least 1.50, more preferably at least 1.55 and most preferably at least 1.60.

The glass transition temperature of the cured polymer composition is preferably less than 37° C., more preferably less then 25° C., and most preferably less than 15° C.

The intraocular lenses according to the invention that are constructed from the materials of the present invention can be of any design capable of being rolled or folded into a small cross section that can fit through a relatively smaller incision. For example, the intraocular lenses can be of what is known as a one piece or multi-piece design, and comprise optic and haptic components. The optic is that portion which serves as the lens. The haptics are attached to the optic and hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the intraocular lens.

EXAMPLE 1

Experimental

The HRI Monomers were synthesized as described below. Their purity was typically 95+%. Other ingredients were purchased off the shelf from outside vendors. Typically 99+% quality materials were used. Synthesis was performed in suitable laboratory glassware. Blue light irradiations for curing were performed using a suitable blue light source under a suitable atmosphere at RT (Room Temperature).

Synthesis of the HRI monomer
2-(1,3-bis(phenylthio)propan-2-yloxy)ethylacrylate

Synthesis of the precursor 1,3-bis(phenylthio)propan-2-ol.

Thiophenol (54.1 mL, 529.1 mmol, 2.0 eq) was added to a threeneck flask and cooled in an ice/water bath, under a nitrogen atmosphere. KOH (29.68 g, 529.1 mmol, 2.0 eq) was dissolved in isopropanol (600 mL) and added to the thiophenol. Epichlorohydrin I (20.7 mL, 264.5 mmol, 1.0 eq) was added drop wise in 20 min. An exothermic reaction was observed, and the temperature was kept below 28° C. A white precipitate formed during addition. The mixture was heated at 65° C. for 1 h. The mixture was poured in aq. 20% citric acid sol. (500 mL). t-Butylmethyl ether (500 mL) was added and the layers were separated. The water layer was extracted with t-butylmethyl ether (250 mL). The combined organic layers were washed subsequently with brine (250 mL), sat. aq. NaHCO$_3$ sol. (500 mL) and brine (500 mL), dried over Na$_2$SO$_4$ and concentrated in vacuo yielding a yellow oil.

To be Able to Incorporate a Spacer Group in the Previous Alcohol, an Ethyl Ester Protected Ethylenic Spacer Group was Used.

The alcohol 1,3-bis(phenylthio)propan-2-ol (50 g, 180.9 mmol, 1.0 eq) and ethyl bromoacetate (30 mL, 271.3 mmol, 1.5 eq) were added to a threeneck flask and dissolved in acetonitril (500 mL), under nitrogen atmosphere. CsCO$_3$ (88.4 g, 271.3 mmol, 1.5 eq) was added. The mixture was warmed to 65° C. and was warmed at this temperature overnight. Water (500 mL) and ethylacetate (250 mL) were added and the layers were separated. The water layer was extracted with ethyl acetate (2×250 mL). The combined organic layers were washed with brine (500 mL), dried over Na$_2$SO$_4$ and concentrated in vacuo to provide 72 g of a brown oil. Purification by column chromatography (2 kg silica, eluent 0 to 10% EtOAc in heptane) yielded 53 g (81%) of a colourless oil.

Then the Ethylester Protection was Removed to Yield the Spacer Modified Alcohol.

LiAlH$_4$ pallets (8.4 g, 220.2 mmol 1.5 eq) were suspended in THF (700 mL), under nitrogen atmosphere. The mixture was cooled in an ice/water bath to 0° C. Then the ethyl ester protected spacer modified alcohol (53 g, 146.8 mmol, 1.0 eq) was dissolved in THF (300 mL) and added drop wise in 80 min to the mixture. After 1.5 hours at 0° C., 20% aq. KOH sol. (39 mL) was added drop wise. After addition the mixture was warmed to room temperature and filtered over Celite. The filter cake was rinsed with THF (250 mL). The filtrate was concentrated in vacuo yielding 42 g of a light yellow oil. Purification by column chromatography (1.2 kg silica, eluent 0 to 40% EtOAc in heptane) provided 31 g (66%) of a colorless oil.

Synthesis of the Monomer.

The spacer modified alcohol (10 g, 31.25 mmol, 1.0 eq) and some crystals methoxyphenol were dissolved in THF (150 mL). Et$_3$N (7.5 mL, 53.13 mmol, 1.7 eq) was added and the solution was cooled to 0° C. with an ice/water bath. Acrylolyl chloride (3.8 mL, 46.88 mmol, 1.5 eq) was added drop wise in 24 min, an exothermic reaction was observed and the temperature was kept below 3° C. A white precipitate is formed during addition. Ethyl acetate (200 mL) and water (250 mL) were added and the layers were separated. The water layer was extracted with ethylacetate (150 mL). The combined organic layers were washed with brine (200 mL), dried over Na$_2$SO$_4$ and concentrated in vacuo to provide 5.3 g of a light brown oil. Purification by column chromatography yielded 4.3 g (37%) of a colourless oil which changed into a white solid overnight. The solid was washed with pentane. The monomer was stabilised with 100 ppm mono-methylether hydroquinone. The identity of the monomer was confirmed by NMR and HPLC-MS.

Formulation Using a HRI Monomer.

The HRI monomer 2-(1,3-bis(phenylthio)propan-2-yloxy)ethylacrylate (M4) was formulated in the following composition under subdued light conditions to avoid premature decomposition of the photoinitiator:

| Material | Wt. % |
|---|---|
| M4 | 90.8 |
| EGDMA* | 7.5 |
| UV-blocker** | 1.5 |
| Irg 819*** | 0.2 |

*Ethylene Glycol Di Methacrylate
**A methacrylate modified benzotriazole based material from Sigma-Aldrich
***A phosphineoxide based photoinitiator from Ciba Specialty Chemicals After complete dissolution of all materials the formulation was ready for use.

Castmoulding

The photocurable HRI monomer containing composition as prepared previously was added to a polymeric castmould consisting of a lower and a upper half enclosing a space in the form of an IOL moulding. The mould was irradiated with blue light under suitable conditions for the appropriate amount of time. After opening of the mould the IOL moulding was removed and inspected for quality. It was found that the moulding consisted of an optically transparent material with the desired properties for a suitable IOL material. The moulding did not tear on folding, and returned to the original dimensions when the folding force was released. Folding marks were not visible after folding, while elongation was about 150%.

The invention claimed is:

1. A high refractive index monomer according to formula (I):

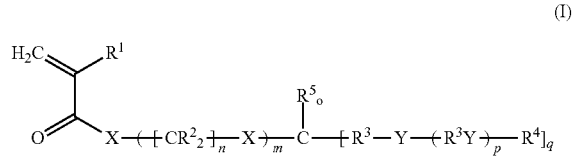

wherein:
$R^1$ is H or CH$_3$;
X is O or S;
$R^2$ is independently H or linear or branched C$_1$-C$_6$ alkyl;
n=3 to 10;
m=1- 10;
$R^3$ is linear or branched C$_1$-C$_3$ alkylene;
Y is O or S;
p=0- 5;
$R^4$ is C$_6$-C$_{18}$ aryl or heteroaryl;
q is 2 or 3;
o is 0 or 1;
when q=2, then o is 1;
when q=3; then o is 0; and
$R^5$ is independently H or linear or branched C$_1$-C$_6$ alkyl.

2. The high refractive index monomer according to claim 1, wherein n is 3-5.

3. The high refractive index monomer according to claim 1, wherein m=1-5.

4. The high refractive index monomer according to claim 1, wherein X is O.

5. The high refractive monomer according to claim 1, wherein Y is S.

6. The high refractive index monomer according to claim 1, wherein p is 0.

7. The high refractive index monomer according to claim 1, wherein q is 2 and o is 1.

8. The high refractive index monomer according to claim 1, wherein $R^5$ is H.

9. The high refractive index monomer according to claim 1, wherein $R^4$ is phenyl.

10. The high refractive index monomer according to formula (II):

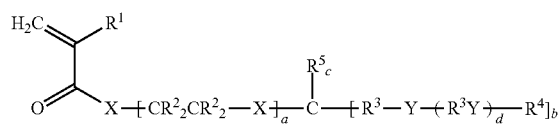

(II)

wherein:
$R^1$ is H or $CH_3$;
X is O or S;
$R^2$ is independently H or linear or branched $C_1$-$C_6$ alkyl;
a=1 to 5;
$R^3$ is linear or branched $C_1$-$C_3$ alkylene;
Y is O or S;
d=0-5;
$R^4$ is $C_6$-$C_{18}$ aryl or heteroaryl;
b is 2 or 3;
c is 0 or 1;
when b=2, then c is 1;
when b=3; then c is 0; and
$R^5$ is independently H or linear or branched $C_1$-$C_6$ alkyl.

11. The high refractive index monomer according to claim 10, wherein a is 1 or 2.

12. The high refractive index monomer according to claim 10, wherein d is 0.

13. The high refractive index monomer according to claim 10, wherein b is 2 and c is 1.

14. The high refractive index monomer according to claim 10, wherein X is O.

15. The high refractive monomer according to claim 10, wherein Y is S.

16. The high refractive index monomer according to claim 10, wherein $R^5$ is H.

17. The high refractive index monomer according to claim 10, wherein $R^4$ is phenyl.

18. A polymer comprising:
(a) a high refractive index monomer according to formula (I):

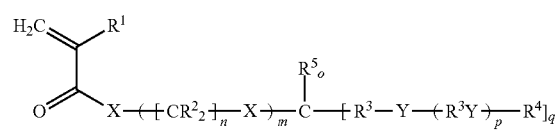

(I)

wherein:
$R^1$ is H or $CH_3$;
X is O or S;
$R^2$ is independently H or linear or branched $C_1$-$C_6$ alkyl;
n=3 to 10;
m=1-10;
$R^3$ is linear or branched $C_1$-$C_3$ alkylene;
Y is O or S;
p=0-5;
$R^4$ is $C_6$-$C_{18}$ aryl or heteroaryl;
q is 2 or 3;
o is 0 or 1;
when q=2, then o is 1;
when q=3; then o is 0; and
$R^5$ is independently H or linear or branched $C_1$-$C_6$ alkyl; or
(b) a high refractive index monomer according to formula (II):

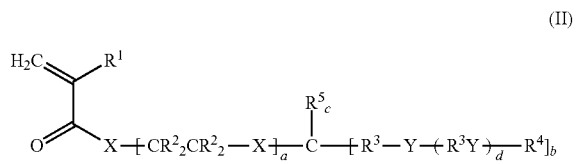

(II)

wherein:
$R^1$ is H or $CH_3$;
X is O or S;
$R^2$ is independently H or linear or branched $C_1$-$C_6$ alkyl;
a=1 to 5;
$R^3$ is linear or branched $C_1$-$C_3$ alkylene;
Y is O or S;
d=0-5;
$R^4$ is $C_6$-$C_{18}$ aryl or heteroaryl;
b is 2 or 3;
c is 0 or 1;
when b=2, then c is 1;
when b=3; then c is 0; and
$R^5$ is independently H or linear or branched $C_1$-$C_6$ alkyl,
wherein said polymer have a glass transition temperature $T_g$ of less than 25° C.

19. The polymer according to claim 18 comprising a crosslinked homopolymer comprising the high refractive index monomers according to formulas (I) or (II).

20. The polymer according to claim 18 comprising a crosslinked copolymer comprising the high refractive index monomers according to formulas (I) or (II), at least a second acrylic monomer, and a crosslinking monomer.

21. The polymer according to claim 20, wherein the second acrylic monomer is represented by formula (VIII):

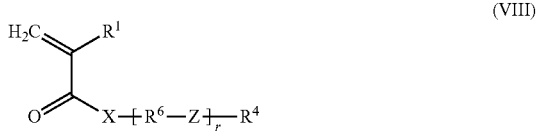

(VIII)

wherein:
$R^1$ is H or $CH_3$;
$R^4$ is $C_6$-$C_{18}$ aryl or heteroaryl;
$R^6$ is substituted or unsubstituted $C_1$-$C_6$ alkylene;
X is as defined above;
Z is O, S or a direct bond; and
r is 0, 1, 2 or 3.

22. The polymer according to claim 20, wherein the crosslinking monomer is a multifunctional (meth)acrylate monomer which comprises at least two (meth)acrylate moieties.

23. The polymer according to claim 20, wherein the crosslinking monomer is represented by the general formula (IX):

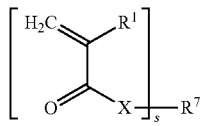

(IX)

wherein:

$R^1$ is H or $CH_3$;

$R^7$ is substituted or unsubstituted $C_1$-$C_{300}$ alkyl, aryl, alkaryl, arylalkyl or heteroaryl;

X is as defined above; and s=2, 3 or 4.

24. An intraocular lens comprising the polymer according to claim 18.

* * * * *